United States Patent
Bethel

[11] Patent Number: 5,738,831
[45] Date of Patent: Apr. 14, 1998

[54] BED LINEN DEODORIZER

[76] Inventor: Fredrick U. Bethel, 178 Hermer Cir. N.W., Atlanta, Ga. 30311

[21] Appl. No.: 847,325

[22] Filed: Apr. 23, 1997

Related U.S. Application Data

[63] Continuation of Ser. No. 559,175, Nov. 13, 1995, abandoned, which is a continuation of Ser. No. 247,660, May 23, 1994, abandoned.

[51] Int. Cl.$^6$ ...................................................... A61L 9/04
[52] U.S. Cl. ................... 422/120; 422/5; 239/36; 239/56
[58] Field of Search ...................... 422/4, 5, 120, 422/122, 123; 239/53–54, 56–57, 34, 36

[56] References Cited

U.S. PATENT DOCUMENTS

| | | | |
|---|---|---|---|
| 877,309 | 1/1908 | Emerson | 422/5 X |
| 2,085,991 | 7/1937 | Minor | 422/5 X |
| 2,585,339 | 2/1952 | Miller | 422/124 |
| 2,614,820 | 10/1952 | Boydjieff | 422/124 X |
| 4,084,732 | 4/1978 | Dearling | 222/402 |
| 4,283,011 | 8/1981 | Spector | 239/57 X |
| 4,341,348 | 7/1982 | Dearling | 239/34 |
| 4,367,203 | 1/1983 | Landsberger | 422/5 X |
| 4,374,571 | 2/1983 | Hirvela | 239/57 X |
| 4,493,011 | 1/1985 | Spector | 362/96 |
| 4,571,485 | 2/1986 | Spector | 219/276 |
| 4,595,564 | 6/1986 | Spector et al. | 422/125 |
| 4,708,851 | 11/1987 | Von Loringhoven | 422/123 |
| 4,744,514 | 5/1988 | Gadoua | 239/36 |
| 4,869,407 | 9/1989 | Booth, Jr. | 222/633 |
| 5,163,616 | 11/1992 | Bernarducci | 239/35 |
| 5,230,867 | 7/1993 | Kunze et al. | 422/123 |
| 5,234,162 | 8/1993 | Sullivan | 239/56 |
| 5,299,335 | 4/1994 | Ivester et al. | 239/56 X |

*Primary Examiner*—Hien Tran

[57] ABSTRACT

A device for deodorizing and freshening a bed mattress, linens, and the air space thereabout including a pliable base, an interior pad positioned on the base and having aromatic fragrance applied thereto, and a cover mounted on the base so as to cover the pad, all forming a sleek, pliable design with minimal, if any, obstruction to a user of the mattress. The base is provided with side vents and the cover is made of a spongy, porous material so as to aid in aromatic dispersement of the fragrance applied to the interior pad.

7 Claims, 5 Drawing Sheets

5,738,831

BED LINEN DEODORIZER

This is a continuation of application Ser No. 08/559,175 filed on Nov. 13, 1995, now abandoned, which is a continuation of application Ser. No. 08/247,660 filed on May 23, 1994, now abandoned.

BACKGROUND OF THE INVENTION

1. Field of the Invention

The present invention generally relates to a fragrance emitting device. In particular, the invention relates to a fragrance emitting device which may be positioned on the mattress of a bed to freshen and deodorize the mattress and linens placed thereon with minimal detection by the mattress user.

2. Description of the Prior Art

Various types of air-freshening devices are known and available for dispensing a specific aroma to the ambient. These prior art devices include aerosol cans with fragrances sprayed therefrom and bottles with liquids which are dispensed therefrom to aromatize the air via a permeable cloth material housed in and extending from the bottle. These devices are generally inappropriate for applications wherein potential contact with a persons' skin is involved. Thus, these well known devices would not be appropriate for use in the environment to which the present invention is directed, namely bedding and linen.

U.S. Pat. No. 5,230,867 to Kunze et al. discloses a fragrance releasing cartridge which comprises a polyester pad sealed within a housing by an air-permeable membrane. The housing includes an opening defined by a lip portion, a shoulder spaced apart from the lip portion for supporting and attaching the membrane thereto, and a recess having a perimeter defined by the shoulder. So constructed, the membrane secures the pad member in the recess. This prior art device has a relatively large, bulky construction which would tend to make it inappropriate for mounting on a mattress without detection.

U.S. Pat. No. 4,493,011 to Spector discloses an aroma disc for a table lamp comprising a circular housing with a central opening for mounting on the lamp shade support of the lamp and an interior pad impregnated with a liquid fragrance. The housing also has a circular array of openings which define ports to expose the pad. When the lamp is turned on, heated air currents from the light bulb penetrate the ports and pass through the pad to emit an aroma throughout the room. This prior art device requires heat in order to produce an aromatic effect. In addition, the disc is comprised of a metal material which would tend to present an uncomfortable interference if placed on a mattress. U.S. Pat. No. 4,869,407 to Booth, Jr. et al. discloses an air-freshener apparatus having a rigid base which contains a fragrance source and an accordion-type housing which allows air to flow over the fragrance source and emit a fragrance from breather holes when the housing is depressed. Because the base is made of a rigid composition, it too, like the prior art devices discussed above, is inappropriate for use in conjunction with a mattress and bedding.

Thus, there is a need for an air-freshening device which is designed to permit little, if any, detection when installed on a mattress. It is to the provision of such a device that the present invention is primarily directed.

SUMMARY OF THE INVENTION

The present invention meets the needs identified above by providing a bed linen deodorizer which may be mounted on a mattress and is constructed to minimize detection and interference with the user of the mattress. The bed linen deodorizer of the present invention comprises a base made of a pliable plastic material, a fragrance-containing pad designed to fit neatly within the base, and a cover made of a spongy material which fits on top of the base and holds the pad in place. Each component of the bed linen deodorizer is designed to permit easy permeation of a fragrance throughout the air space around and between a mattress and linens placed thereon. For example, the base contains ventilation openings, the cover is made of a spongy material, and the cover optionally has a ventilation opening, all of which aid in aromatic dispersement.

Accordingly, it is a primary object of the present invention to provide a bed linen deodorizer which may be mounted on a mattress while minimizing discomfort to individuals sitting or reclining on the mattress.

It is another object of the present invention to provide a fragrance dispensing device which eliminates odors and freshens the air space around and between a mattress and the covers placed thereon.

It is still another object of the present invention to provide an air-freshening apparatus which is compact in size.

Yet another object of the present invention is to provide an air-freshening device which is easy to manufacture and inexpensive in cost.

These and other objects, features and advantages of the present invention will become apparent upon reading the following specification in conjunction with the accompanying drawing figures.

DETAILED DESCRIPTION

The present invention is directed to an apparatus which is capable of eliminating odors or masking the effects thereof while at the same time providing a desirable fragrance to the mattress of a bed, bedding and linen placed on the mattress, and the air space between a mattress and the covers placed thereon. In addition, the device of the present invention may provide a fragrance to the air space surrounding a bed and indeed the entire room containing the bed depending upon the strength or concentration of fragrance which is used and the porosity of the covers placed on the bed.

Figure 1:
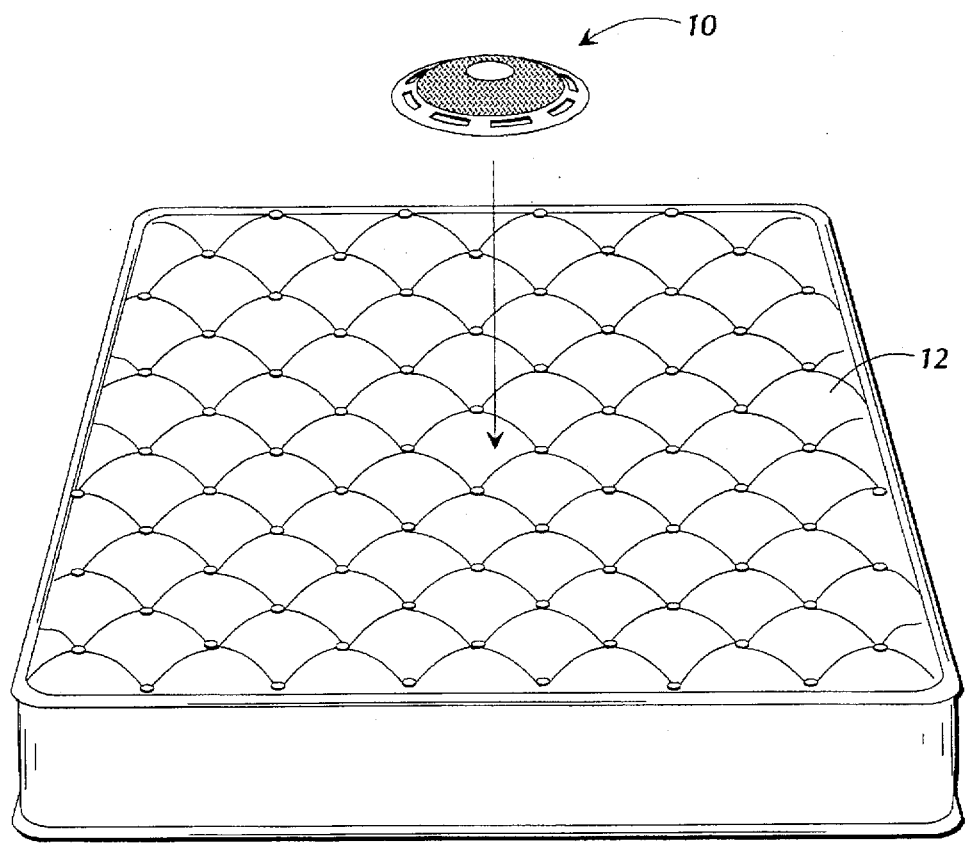
FIG. 1 is a perspective view of a first preferred embodiment of the bed linen deodorizer according to the present invention and shown in the primary environment in which it is intended to be used, namely, on a mattress.
Figure 2:
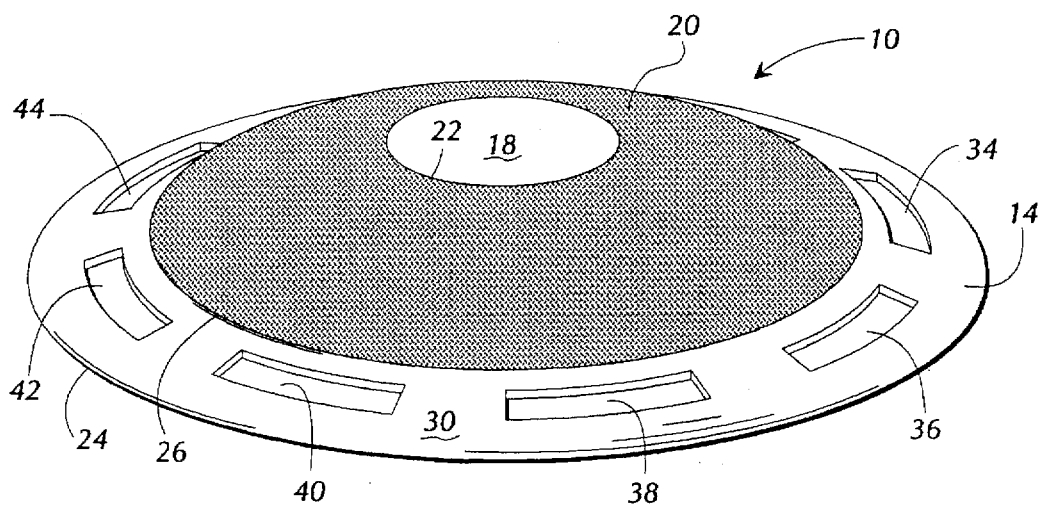
FIG. 2 is another perspective view of the bed linen deodorizer of FIG. 1.

Referring now in detail to the drawing figures, wherein like reference numbers denote like parts throughout the several views, FIGS. 1 and 2 show a first preferred embodiment of the bed linen deodorizer 10 of the present invention. As illustrated in FIG. 1, the preferred application for the device of the present invention is in conjunction with a mattress 12 and bedding, linen, or covers (not shown) which may be placed on the mattress 12.

Referring now to FIG. 2, a perspective view of the bed linen deodorizer 10 of the present invention is shown in greater detail. As can be seen, the bed linen deodorizer 10 preferably has an overall generally circular or disc-shaped construction. Such a construction tends to minimize bodily detection of the deodorizer 10 when it is placed on a mattress because of the absence of sharp edges. Other features of the present invention also aid in minimizing bodily detection of the bed linen deodorizer 10 by the user of a mattress 12 on which the bed linen deodorizer 10 is used. For example, bed linen deodorizer 10 is preferably formed of a flexible or pliable material which is relatively soft to the touch. In addition, it may be observed from FIG. 2 that the overall construction of bed linen deodorizer 10 is of a generally sleek design having a vertical dimension (thickness) which is substantially smaller than its horizontal dimension (diameter). This feature also aids in minimizing bodily detection of the bed linen deodorizer 10 when installed on a mattress 12. In the first preferred embodiment, the bed linen deodorizer 10 of the present invention has an overall diameter of 3½ inches and an approximate height of 5/16 inch. However, the ranges of dimensions for the bed linen deodorizer 10 of the present invention include an overall diameter of from about 2 inches to about 7 inches and an approximate height of from about ¼ inch to about ½ inch. In this regard, the overall design of the apparatus is quite thin. As used in the claims, "thin" refers to the height being generally about an order of magnitude smaller than the lateral dimension (e.g., the diameter).

Figure 3:
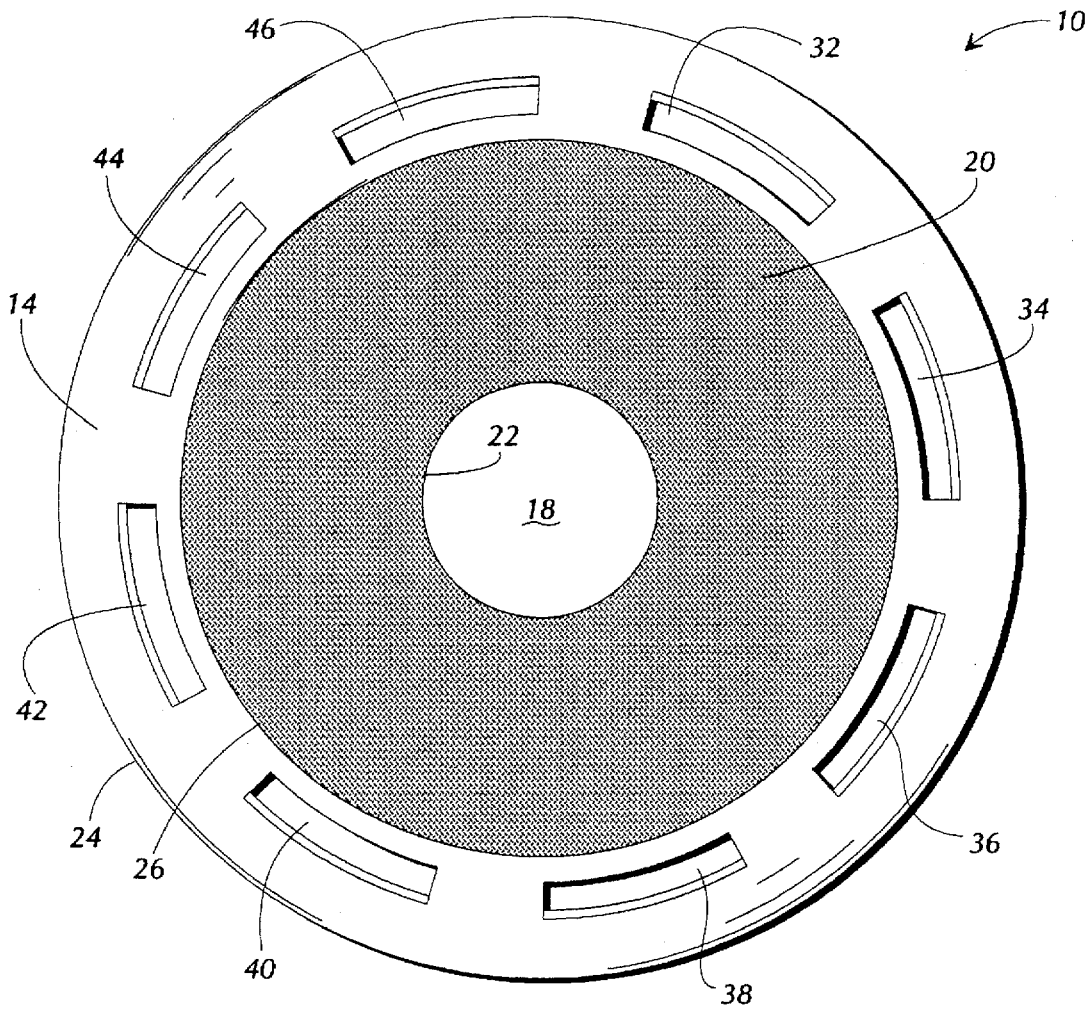
FIG. 3 is a plan view of the bed linen deodorizer of FIG. 1.

Referring now to FIG. 3, a top plan view of the bed linen deodorizer 10 as depicted in FIGS. 1 and 2 is shown. From this perspective, it may be observed that bed linen deodorizer 10 has a generally circular base 14 which has a plurality of side vents 32, 34, 36, 38, 40, 42, 44, 46 disposed about its periphery in a circular fashion between outer edge 24 and inner edge 26 of base 14. Side vents 32, 34, 36, 38, 40, 42, 44, 46 permit a fragrance to be emitted from a pad 18 housed beneath cover 20. Cover 20 is mounted on top of base 14 and has a diameter which is approximately equal to that of the inner edge 26 of base 14. Cover 20 may have a portion defining an optional top vent 22 which may be formed by removing a portion of the material which comprises cover 20. Top vent 22 further increases the aromatic dispersion of fragrance from pad 18 housed under cover 20.

Figure 4:
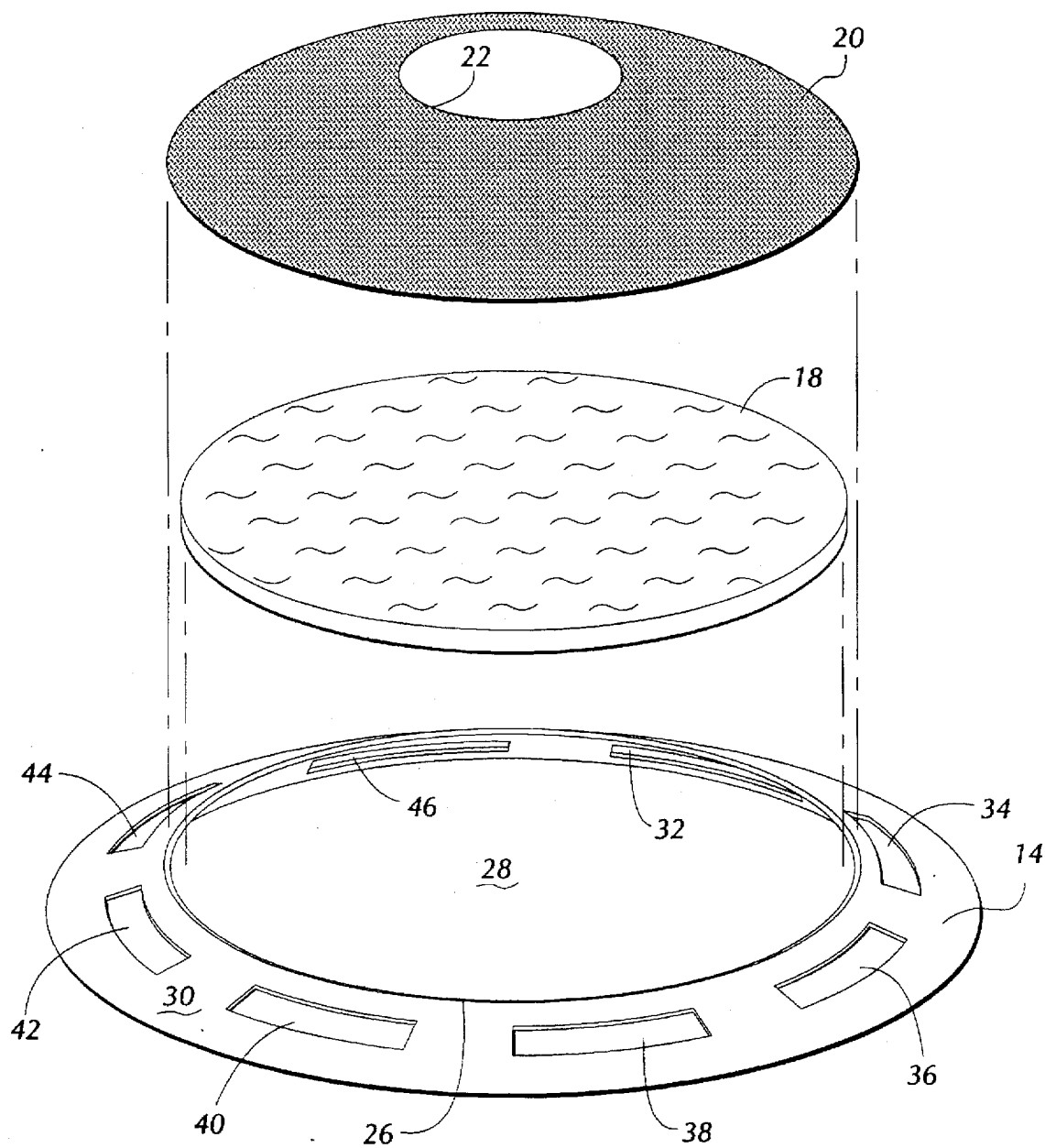
FIG. 4 is an exploded view of the bed linen deodorizer of FIG. 1.

Referring now to FIG. 4, an exploded view of the bed linen deodorizer 10 depicted in FIGS. 1 and 2 is shown. From this view, the three primary components which comprise the bed linen deodorizer 10 of the present invention are depicted. These components are base 14, pad 18, and cover 20. Base 14 has a bottom with an upper surface 28 which is approximately equal in diameter to the outer edge 24 of base 14. Base 14 is preferably a singular integral component which is formed of a lightweight plastic, pliable material. A side wall 30 is formed between outer edge 24 and inner edge 26. Side wall 30 is inclined so as to create approximately a 30° angle between side wall 30 and the upper surface 28 of the bottom of base 14. Such an incline on side wall 30 provides a sleek design for bed linen deodorizer 10 and allows the bed linen deodorizer to go unfelt when placed on a mattress. Although an angle of approximately 30° is preferred, side wall 30 may have an incline of from about 1° to about 45° relative to the upper surface 28 of the bottom of base 14.

A pad 18 is placed within base 14 atop the upper surface 28 of the bottom of base 14. Pad 18 is preferably a disc-shaped, fragrance dispensing fabric, such as compressed cotton, although other materials may be used. In the preferred embodiment, pad 18 is approximately 2½ inches in diameter and 1/16 inch thick. However, the range of thicknesses for pad 18 is from about 1/20 inch to about 1/10 inch and the range of the diameter is from about 1½ inch to about 5 inches. Pad 18 may be provided with any desired fragrance so as to emit the aroma desired by the user of the bed linen deodorizer 10.

Mounted above of pad 18 is a cover 20 which is preferably made of a spongy material. Such a material is porous (i.e., having a plurality of pores) and allows a fragrance to be transmitted from the pad 18 through the cover 20 so as to provide the desired aromatic effect while at the same time avoiding any possible discomfort to a person sitting or reclining on a mattress 12 (FIG. 1 ) on which the bed linen deodorizer 10 is installed. As mentioned above, an optional top vent 22 may be formed in cover 20 by removing a portion of cover 20. Such a vent further aids in aromatic dispersion of fragrance from pad 18.

Figure 5A:
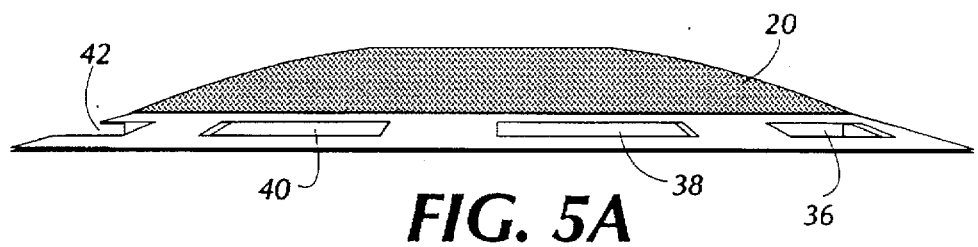
FIG. 5A is a side elevation view of the bed linen deodorizer of FIG. 1.
Figure 5B:
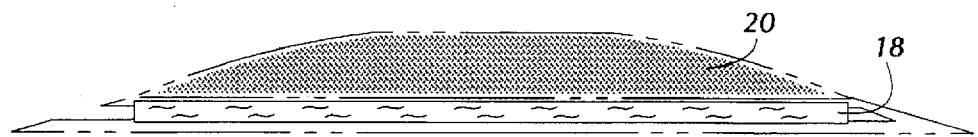
FIG. 5B is a side sectional view of the bed linen deodorizer of FIG. 1.

Referring now to FIGS. 5A and 5B, it may be noted that pad 18 is positioned beneath cover 20 and adjacent to side vents 36, 38, 40, 42. The location of the side vents contributes to lateral dispersement of fragrance applied to pad 18. The number of side vents provided is selected dependent upon the rate at which one wishes to have fragrance dispersed from pad 18.

Figure 6:
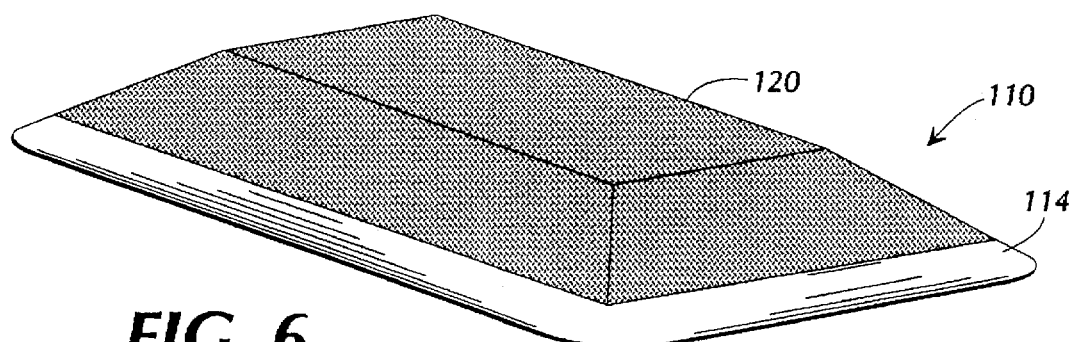
FIG. 6 is a perspective view of a second preferred embodiment of the bed linen deodorizer according to the present invention.
Figure 7:
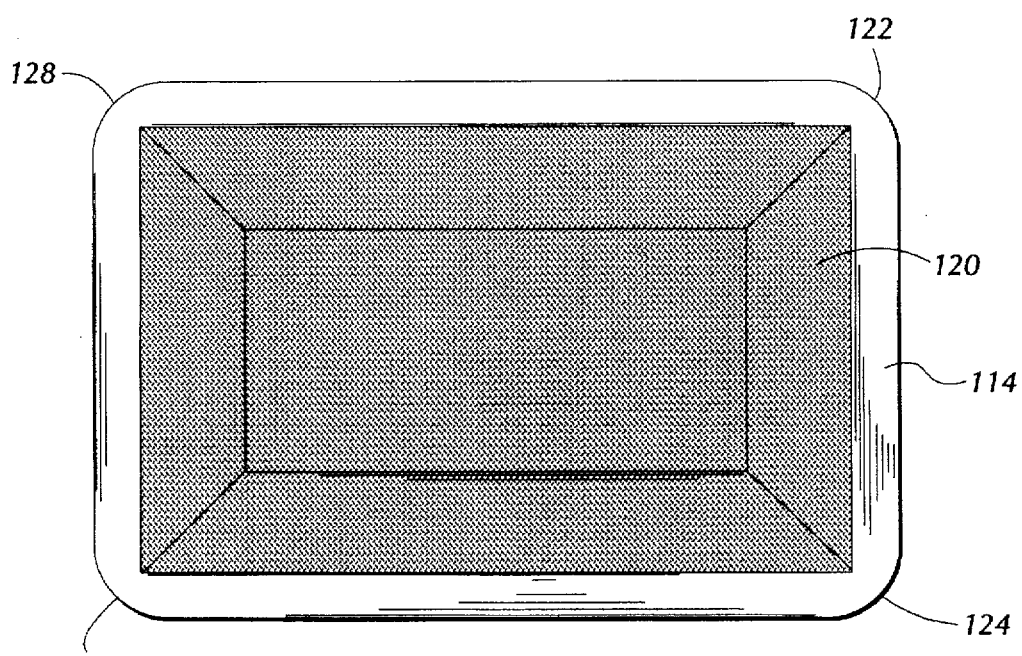
FIG. 7 is a plan view of the bed linen deodorizer of FIG. 6
Figure 8:
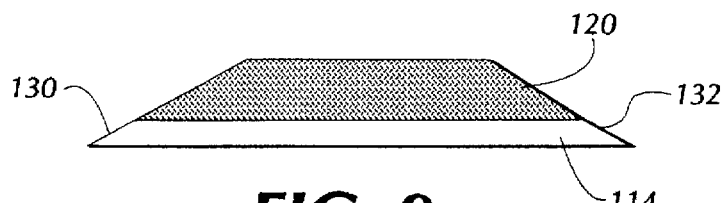
FIG. 8 is a side elevation view of the bed linen deodorizer of FIG. 6.
Figure 9:
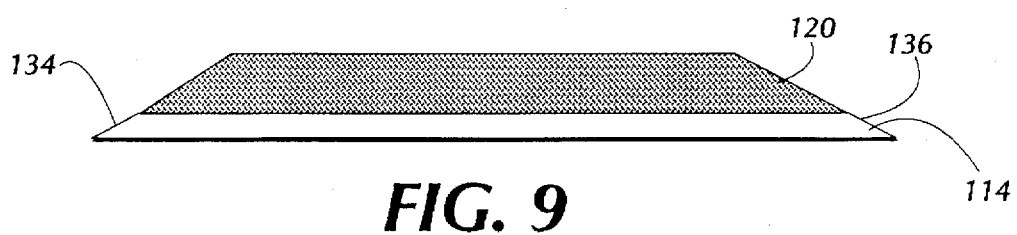
FIG. 9 is a front elevation view of the bed linen deodorizer of FIG. 6.

Referring now to FIGS. 6-9, a second preferred embodiment of the bed linen deodorizer 110 of the present invention is shown. As shown in FIG. 6, the overall shape of the second preferred embodiment is generally pyramidal, having a generally rectangular base 114 (FIG. 7) which has rounded corners 122, 124, 126, 128, inwardly tapering side walls 134, 136 (FIG. 9), an inwardly tapering front wall 130 (FIG. 8), and an inwardly tapering rear wall 132. The overall pyramidal shape of the second preferred embodiment has a truncated top portion in that the cover has a generally flat top. As in the first preferred embodiment, a pad (not shown) having a fragrance applied thereto is positioned between base 114 and cover 120 allowing the fragrance to be emitted from the pad, permeate through cover 120, and freshen the mattress, linens, and surrounding air space with a desired aroma.

Figure 10:
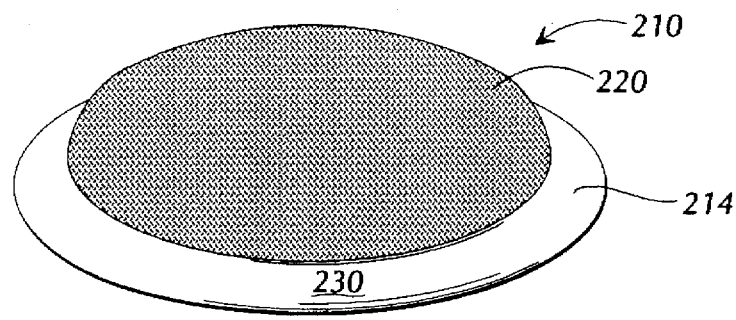
FIG. 10 is a perspective view of a third preferred embodiment of the bed linen deodorizer according to the present invention.
Figure 11:
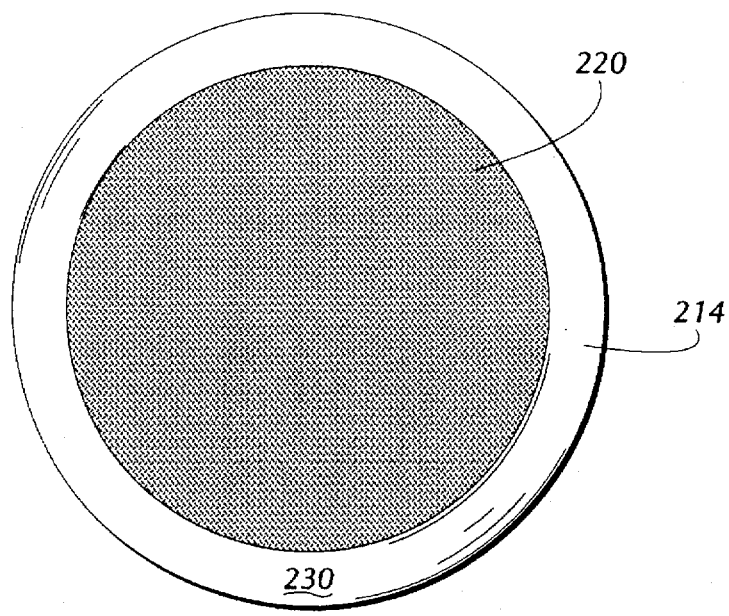
FIG. 11 is a plan view of the bed linen deodorizer of FIG. 10.
Figure 12:
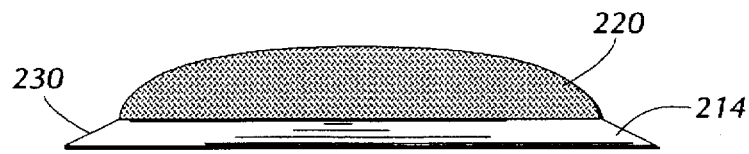
FIG. 12 is an elevation view of the bed linen deodorizer of FIG. 10.

Referring now to FIGS. 10-12, a third preferred embodiment of the bed linen deodorizer 210 of the present invention is shown. As shown in FIG. 12, the cover 220 in the third preferred embodiment is more rounded relative to the first and second preferred embodiments. However, like the first preferred embodiment, the base is generally circular in shape and has an inwardly sloping side wall 230.

The bed linen deodorizer 10 of the present invention is intended to be sold in a plastic wrapper which will allow the fragrance applied to pad 18 to be retained until the bed linen deodorizer is placed in use. The bed linen deodorizer 10 is placed in use by putting it on a mattress 12 as illustrated in FIG. 1. Optionally, the bottom of bed linen deodorizer 10 may be provided with an adhesive such as two-sided tape so as to minimize movement of the bed linen deodorizer 10 on a mattress 12. In use, bed linen deodorizer 10 emits a desired fragrance from pad 18 through side vents 32, 34, 46, 48, 40, 42, 44, 46 of base 14, through pores in the material which comprises cover 20, and optionally through a top vent 22 in cover 20. The movement of air in the vicinity of bed linen deodorizer 10 allows the fragrance in pad 18 to be dispersed in the air space surrounding the bed linen deodorizer 10 of the present invention. Bed linen deodorizer 10 is intended to aromatize and deodorize for approximately 30 days after which time it may be disposed of and replaced.

Although the present invention has been described in detail with respect to preferred embodiments thereof, it will be apparent to those skilled in the art that many modifications, additions, and deletions may be made therein without departing from the scope and spirit of the invention. Therefore, the present invention should not be judged by the specific embodiments set forth herein but rather by the scope and spirit of the invention as set forth in the following claims.

What is claimed is:

1. An apparatus for freshening and deodorizing a bed having a mattress and linens placed on the mattress, and air space around and between the mattress and the linens, the apparatus comprising:

a pliable base for mounting on a mattress, said base having an upper surface, an outer edge, an inner edge positioned above and inwardly relative to said outer edge, and a side wall formed between said outer edge and said inner edge, said side wall being disposed at an incline of about 30° relative to said upper surface of said base and defining a pad-receiving recess, wherein said side wall has a plurality of portions defining side vents through which a fragrance emanates;

a pad mounted above said upper surface of said base and completely within said pad-receiving recess, said pad having a fragrance applied thereto; and a cover mounted toward said inner edge of said base, said cover being formed of sponge for permitting the fragrance to emanate from said pad through said cover whereby the mattress, linens placed on the mattress, and the air space around and between the mattress and linens are freshened and deodorized.

2. The apparatus as recited in claim 1 wherein said cover has a portion defining a top vent through which the fragrance emanates.

3. The apparatus as recited in claim 1 wherein said pad is formed of compressed cotton.

4. The apparatus as recited in claim 1, further comprising attachment means for securing said base to the mattress.

5. The apparatus as recited in claim 4 wherein said attachment means is an adhesive.

6. The apparatus as recited in claim 1 wherein said base is substantially circular in shape.

7. The apparatus as recited in claim 1 wherein said base is substantially rectangular in shape.

* * * * *